United States Patent
Sasaki et al.

(10) Patent No.: US 12,042,483 B2
(45) Date of Patent: Jul. 23, 2024

(54) PROPHYLACTIC AND THERAPEUTIC DRUG FOR NONALCOHOLIC FATTY LIVER DISEASE

(71) Applicant: Kowa Company, Ltd., Nagoya (JP)

(72) Inventors: Yusuke Sasaki, Tokyo (JP); Masato Asahiyama, Shizuoka (JP); Toshiya Tanaka, Tokyo (JP)

(73) Assignee: Kowa Company, Ltd., Nagoya (JP)

( * ) Notice: Subject to any disclaimer, the term of this patent is extended or adjusted under 35 U.S.C. 154(b) by 0 days.

(21) Appl. No.: 17/515,945

(22) Filed: Nov. 1, 2021

(65) Prior Publication Data

US 2022/0054459 A1 Feb. 24, 2022

Related U.S. Application Data

(63) Continuation of application No. 16/477,416, filed as application No. PCT/JP2018/000398 on Jan. 11, 2018, now abandoned.

(30) Foreign Application Priority Data

Jan. 11, 2017 (JP) ................................. 2017-002731

(51) Int. Cl.
 *A61K 31/423* (2006.01)
 *A61P 1/16* (2006.01)
 *A61K 31/7034* (2006.01)
 *A61K 31/7048* (2006.01)

(52) U.S. Cl.
 CPC .............. *A61K 31/423* (2013.01); *A61P 1/16* (2018.01); *A61K 31/7034* (2013.01); *A61K 31/7048* (2013.01)

(58) Field of Classification Search
 CPC .............. A61K 31/423; A61K 31/7034; A61K 31/7048; A61P 35/00; A61P 43/00
 See application file for complete search history.

(56) References Cited

U.S. PATENT DOCUMENTS

| | | | |
|---|---|---|---|
| 2005/0101636 | A1 | 5/2005 | Yamazaki et al. |
| 2008/0045466 | A1 | 2/2008 | Katsuno et al. |

(Continued)

FOREIGN PATENT DOCUMENTS

| | | | |
|---|---|---|---|
| AU | 2014288272 A1 | 1/2016 | |
| EP | 1782828 A1 | 5/2007 | |
| WO | 2005/023777 A1 | 3/2005 | |

(Continued)

OTHER PUBLICATIONS

Second Mexican Office Action of Mexican Patent Application No. MX/a/2019/008317 with an English version of communication received from the Mexican associate.

(Continued)

*Primary Examiner* — San Ming R Hui
(74) *Attorney, Agent, or Firm* — Clark G. Sullivan

(57) ABSTRACT

The present invention addresses the problem of providing a medicinal composition and a drug combination by which nonalcoholic fatty liver disease and nonalcoholic steatohepatitis can be prevented and/or treated. The present invention provides a combination of a peroxisome proliferator-activated receptor (PPAR) α agonist with a sodium glucose cotransporter 2 (SGLT2) inhibitor, which is to be used for preventing and/or treating nonalcoholic fatty liver disease and nonalcoholic steatohepatitis.

11 Claims, 2 Drawing Sheets

(56) References Cited

U.S. PATENT DOCUMENTS

2016/0113953 A1 4/2016 Gannedahl
2016/0136138 A1 5/2016 Shibata et al.

FOREIGN PATENT DOCUMENTS

| WO | 2006/009149 A1 | 1/2006 |
| WO | 2015/005365 A1 | 1/2015 |
| WO | 2016/046311 A1 | 3/2016 |

OTHER PUBLICATIONS

1 Office Action dated Nov. 10, 2022 in Australian Application No. 2018206907.
European Search Report dated Jul. 8, 2022 in European Patent Application No. 18 738 999.4.
J-C Fruchart, "Selective peroxisome proliferator-activated receptora modulators (SPPARMa): the next generation of peroxisome proliferator-ativated receptor a-agnonists", Cardiovascular Diaberology 2013, 12:82 (8 pages).
Hameed, Bilal and Norah Terrault. "Emerging therapies for nonalcoholic fatty liver disease." Clinics in liver disease 20.2 (2016): 365-385.
Suzuki, M., et al. "Tofogliflozin, a sodium/glucose cotransporter 2 inhibitor, attenuates body weight gain and fat accumulation in diabetic and obese animal models." Nutrition & diabetes 4.7 (2014): e125, pp. 1-9.
Honda, Yasushi, et al. "The selective SGLT2 inhibitor ipragliflozin has a therapeutic effect on nonalcoholic steatohepatitis in mice." PLoS One 11.1 (2016): e0146337, pp. 1-13.
Dossi, Camila G., et al. "Reversal of high-fat diet-induced hepatic steatosis by n-3 LCPUFA: role of PPAR-? and SREBP-1c." The Journal of nutritional biochemistry 25.9 (2014): 977-984.
Zúñiga, Jessica, et al. "N-3 PUFA supplementation triggers PPAR-? activation and PPAR-?/NF-?B interaction: anti-inflammatory implications in liver ischemia-reperfusion injury." PloS one 6.12 (2011): e28502, pp. 1-9.
Svegliati-Baroni, Gianluca, et al. "A model of insulin resistance and nonalcoholic steatohepatitis in rats: role of peroxisome proliferator-activated receptor-? and n-3 polyunsaturated fatty acid treatment on liver injury." The American journal of pathology 169.3 (2006): 846-860.
English translation summary of Japanese International Preliminary Report on Patentability dated Jul. 25, 2019 issued In counterpart JP Application PCT/JP2018/000398.
Written Opinion issued in corresponding International Application No. PCT/JP20018/000398 dated Mar. 27, 2018, 8 pages.
Chalasani, Naga, et al. "The diagnosis and management of non? alcoholic fatty liver disease: Practice Guideline by the American Association for the Study of Liver Diseases, American College of Gastroenterology, and the American Gastroenterological Association." Hepatology 55.6 (2012): 2005-2023.
Musso, G., Cassader, M., & Gambino, R. (2016). Non-alcoholic steatohepatitis: emerging molecular targets and therapeutic strategies. Nature reviews Drug discovery, 15(4), 249-274.
Day, Christopher P., and Oliver FW James. "Steatohepatitis: a tale of two "hits"?." (1998): 842-845.
Tilg, Herbert, and Alexander R. Moschen. "Evolution of inflammation in nonalcoholic fatty liver disease: the multiple parallel hits hypothesis." Hepatology 52.5 (2010): 1836-1846.
Matteoni, Christi A., et al. "Nonalcoholic fatty liver disease: a spectrum of clinical and pathological severity." Gastroenterology 116.6 (1999): 1413-1419.
Fernández-Miranda, C., et al. "A pilot trial of fenofibrate for the treatment of non-alcoholic fatty liver disease." Digestive and Liver Disease 40.3 (2008): 200-205.
Fujii, Masato, et al. "A murine model for non-alcoholic steatohepatitis showing evidence of association between diabetes and hepatocellular carcinoma." Medical molecular morphology 46.3 (2013): 141-152.
NAFLD/NASH Clinical Practice Guideline, 2014 of the Japanese Society of Gastroenterology, pp. i-xxii and 1-140, with English translation of pp. 96-104.
Sasaki, Yusuke et al., "Development on pemafibrate of selective PPAR? modulator (SPPARM?)", Prog. Med., Sep. 2017, vol. 37, No. 9, pp. 1033-1041.
Wilkison W. et al. Abstract O047. International Liver Congress; Apr. 22-26, 2015.
Office Action issued in Russian application No. 2019123735/04 dated Mar. 26, 2021.
English translation of Office Action issued in Russian application No. 2019123735/04 dated Mar. 26, 2021.
International Statistical Classification of Diseases and Related Health Problems. 10th Revision (ICD-10). vol. 1 (Part 1). Geneva: World Health Organization, 1995.—698 p., pp. 597-602.
English translation of International Statistical Classification of Diseases and Related Health Problems. 10th Revision (ICD-10). vol. 1 (Part 1). Geneva: World Health Organization, 1995.—698 p., pp. 597-602.
Mashkovskiy M.D., Lekarstvennye sredstva (Medicaments).—16th edition, revised and updated.—M.: Novaya volna, 2012.—1216 p., pp. 8, 12, 13.
English translation of Mashkovskiy M.D., Lekarstvennye sredstva (Medicaments).—16th edition, revised and updated.—M.: Novaya volna, 2012.—1216 p., pp. 8, 12, 13.
Florence A.T., Attwood D. Physicochemical principles of pharmacy. 3rd ed.—1998.—Easton, Bristol: Aarontype Limited.—564 p., pp. 18-21, section 1.4.1.
Office Action dated Aug. 10, 2023 in corresponding Russian Application No. 2019123735/04—English language translation provided.
J.H. Han et al., "The beneficial effects of empagliflozin, an SGLT2 inhibitor, on atherosclerosis in ApoE mice fed a western diet", Diabetologia (2017) 60:364-376.

[FIG. 1]
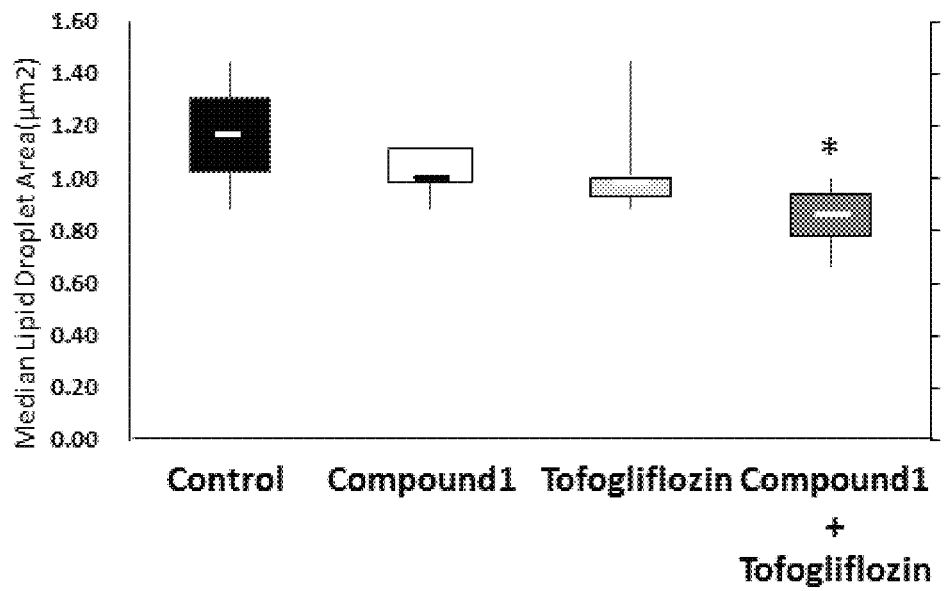
[FIG. 2]
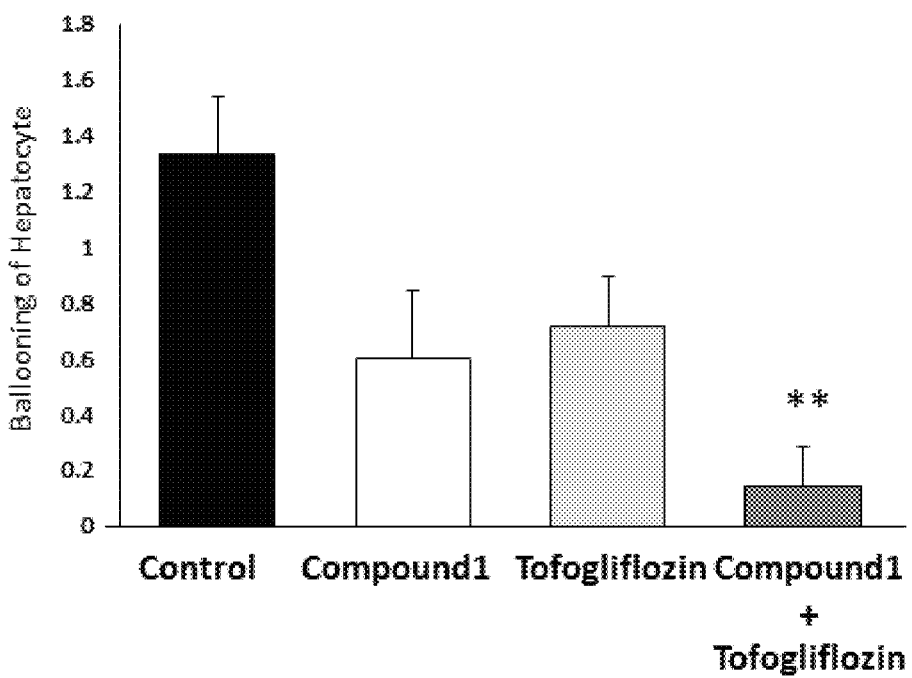

[FIG. 3]
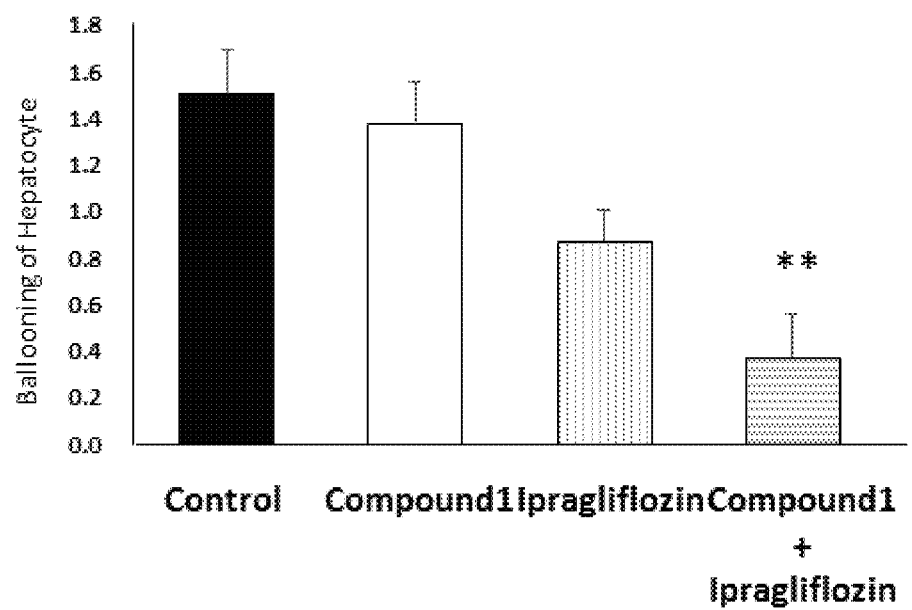

PROPHYLACTIC AND THERAPEUTIC DRUG FOR NONALCOHOLIC FATTY LIVER DISEASE

CROSS-REFERENCE TO RELATED APPLICATIONS

This application is a continuation application of U.S. application Ser. No. 16/477,416, filed on Jul. 11, 2019, which is a U.S. national phase entry of International Application No. PCT/JP2018/000398, filed on Jan. 11, 2018 which claims the benefit of Japanese Patent Application No. 2017-002731 filed Jan. 11, 2017. The entire contents of these applications are incorporated herein by reference in their entirety.

TECHNICAL FIELD

The present invention relates to a prophylactic and/or therapeutic agent for nonalcoholic fatty liver disease.

BACKGROUND ART

Nonalcoholic fatty liver disease (NAFLD) is a fatty liver disorder not associated with alcoholic hepatitis or viral hepatitis. NAFLD is estimated to affect about 30% of the general population. NAFLD is a generic term for a range of conditions from simple steatosis to nonalcoholic steatohepatitis (NASH). Simple steatosis is accumulation of fat in hepatocytes and has a relatively good prognosis. NASH includes both a fatty liver and liver inflammation and may lead to a relatively severe condition such as fibrosis of liver tissue, liver cirrhosis or hepatocellular carcinoma. The treatment for viral hepatitis such as hepatitis C has made rapid progress recently and therefore the number of patients with liver cancer caused by virus is expected to decrease in the future. In contrast, the number of patients with liver cancer based on NASH is expected to increase (Non-Patent Documents 1, 2 and 3).

NAFLD is considered to develop by a widely known mechanism of "two hit theory" in which NAFLD progresses from the stage of accumulation of fat in hepatocytes to the stage of liver inflammation/fibrosis (Non-Patent Document 4). Furthermore, "multiple-parallel hit theory" has been proposed recently, in which various factors are involved in progression of NAFLD in parallel (Non-Patent Document 5). In diagnosis of NASH, key factors are hepatocyte ballooning, Mallory-Denk body and fibrosis. The NAFLD/NASH Clinical Practice Guideline of the Japanese Society of Gastroenterology defines the pathological diagnostic criterion for NASH as "NAFLD having hepatocyte ballooning degeneration with inflammation in addition to macrovesicular fatty change".

Matteoni et al. classified NAFLD patients into four stages based on the pathological findings in light of their prognosis, and defined Types 3 and 4 as NASH (Non-Patent Documents 3 and 6). Hepatocyte enlargement and ballooning degeneration are pathological findings that indicate fat accumulation causes degeneration of the cytoskeleton. These findings are key diagnosis criteria for NASH.

Treatment for NAFLD bases principally on care about obesity, diabetes, dyslipidemia and hypertension through improvement of lifestyle such as diet therapy and exercise therapy. In addition to improvement of lifestyle, drug treatments are performed in clinical practice. Drugs for the treatment target insulin resistance, lipid metabolism disorder, hypertension or oxidative stress. Drugs used for insulin resistance include insulin sensitizing drug such as thiazolidine-based derivatives (pioglitazone, rosiglitazone, etc.) that are ligands for a nuclear receptor PPARγ involved in enhancement of insulin sensitivity, or biguanide-based drugs (metformin etc.). Drugs used for lipid metabolism disorders include fibrate-based drugs (fenofibrate, bezafibrate, etc.) that are PPARα agonists, statin-based preparations or intestinal cholesterol reabsorption inhibitors (ezetimibe etc.). Drugs used for hypertension include angiotensin II type 1 receptor antagonists (ARBs) (Non-Patent Documents 1 and 3).

In addition, for oxidative stress, drugs used as an antioxidant include vitamin E.

An appropriate regimen for a patient may be selected depending on underlying disease from these drug treatments. However, any drug treatment requires further examination. Unfortunately, NAFLD has no currently available established drug treatment.

Regarding fibrate-based drugs, fenofibrate is reported to be investigated for the effect on NAFLD in clinical trials (Non-Patent Document 7). In addition, Patent Document 1 discloses that (R)-2-[3-[[N-(benzoxazol-2-yl)-N-3-(4-methoxyphenoxy)propyl]aminomethyl]phenoxy]butyric acid or a salt thereof, or a solvate thereof has a selective PPARα activating effect, and Patent Document 2 discloses that the compound is useful for prevention and treatment of nonalcoholic fatty liver disease. Meanwhile, as for sodium glucose cotransporter 2 (SGLT2) inhibitors, remogurifurojin has been performed clinical investigation and is reported to have curative effect on NASH (Non-Patent Document 8). Along with a worldwide increase in patients with metabolic syndrome, the number of NASH patients is also predicted to increase. Since NASH is thought to be a cause of nonviral hepatocellular carcinoma, which is a major factor for cancer-related death (Non-Patent Document 9), more effective treatment is desired to be established.

CITATION LIST

Patent Document

Patent Document 1: WO 2005/023777
Patent Document 2: WO 2015/005365

Non-Patent Document

Non-Patent Document 1: Chalasani N. et al. Hepatology, 55, 2005-23 (2012)
Non-Patent Document 2: Musso G. et al. Nat. Rev. Drug Discov. 15 (4), 249-74 (2016.1)
Non-Patent Document 3: NAFLD/NASH Clinical Practice Guideline, 2014 of the Japanese Society of Gastroenterology
Non-Patent Document 4: Day C P. et al, Gastroenterology, 114 (4), 842-5 (1998)
Non-Patent Document 5: Tilg H. et al. Hepatology, 52, 1836-46 (2010)
Non-Patent Document 6: Matteoni C A. et al. Gastroenterology, 116, 1413-9 (1999)
Non-Patent Document 7: Fernandez-Miranda C. et al. Dig. Liver Dis., 40, 200-5 (2008)
Non-Patent Document 8: Wilkison W. et al. Abstract 0047. International Liver Congress; Apr. 22-26, 2015
Non-Patent Document 9: Fujii M. et al. Med. Mol. Morphol, 46, 141-52 (2013)

SUMMARY OF INVENTION

Technical Problem

An object of the present invention is to provide a pharmaceutical composition and/or a combination of drugs that have preventing and/or improving effect on enlargement of lipid droplets in hepatocytes and/or ballooning of hepatocytes and therefore are capable of preventing and/or treating NAFLD and NASH.

Solution to Problem

In view of the above-mentioned problems, in order to find a mean useful for prevention and/or treatment of nonalcoholic fatty liver disease (NAFLD), in particular, severe nonalcoholic steatohepatitis (NASH), the present inventors have conducted intensive studies using a NASH-HCC mouse model. They have found that a combination of (R)-2-[3-[[N-(benzoxazol-2-yl)-N-3-(4-methoxyphenoxy) propyl]aminomethyl]phenoxy]butyric acid (hereinafter, also referred to as Compound 1) that is a PPARα agonist with an SGLT2 inhibitor, which is disclosed in Expert Opin. Investig. Drugs (2013) 22(4): 463-486 etc., exerts strong effects to reduce the size of lipid droplet in hepatocyte and/or to suppress ballooning of hepatocyte, and as a result, to prevent and/or treat NAFLD and NASH. The present invention has been accomplished on the basis of these findings.

In other words, the present invention relates to a composition, kit or the like, characterized by a combination of a PPARα agonist with an SGLT2 inhibitor. More specifically, the present invention relates to the following items [1] to [52].

[1] A prophylactic and/or therapeutic agent for liver disease, including a combination of a PPARα agonist with an SGLT2 inhibitor.

[2] The prophylactic and/or therapeutic agent according to the item [1], wherein the liver disease comprises nonalcoholic fatty liver disease.

[3] The prophylactic and/or therapeutic agent according to the item [2], wherein the nonalcoholic fatty liver disease comprises nonalcoholic steatohepatitis.

[4] The prophylactic and/or therapeutic agent according to the item [2], having an effect to suppress hepatocyte ballooning in a subject with nonalcoholic fatty liver disease.

[5] The prophylactic and/or therapeutic agent according to the item [1], wherein the liver disease comprises liver cirrhosis or hepatocellular carcinoma.

[6] The prophylactic and/or therapeutic agent according to any of the items [1] to [5], wherein the PPARα agonist is (R)-2-[3-[[N-(benzoxazol-2-yl)-N-3-(4-methoxyphenoxy) propyl]aminomethyl]phenoxy]butyric acid or a salt thereof, or a solvate thereof.

[7] The prophylactic and/or therapeutic agent according to any of the items [1] to [6], wherein the SGLT2 inhibitor is selected from dapagliflozin, canagliflozin, ipragliflozin, empagliflozin, luseogliflozin, tofogliflozin, ertugliflozin, sotagliflozin, bexagliflozin or remogliflozin.

[8] The prophylactic and/or therapeutic agent according to any of the items [1] to [7], being a combination drug.

[9] The prophylactic and/or therapeutic agent according to any of the items [1] to [7], being a kit.

[10] A medicament for use in prevention and/or treatment of liver disease, including a combination of a PPARα agonist with an SGLT2 inhibitor.

[11] The medicament according to the item [10], wherein the liver disease comprises nonalcoholic fatty liver disease.

[12] The medicament according to the item [11], wherein the nonalcoholic fatty liver disease comprises nonalcoholic steatohepatitis.

[13] The medicament according to the item [11], having an effect to suppress hepatocyte ballooning in a subject with nonalcoholic fatty liver disease.

[14] The medicament according to the item [10], wherein the liver disease comprises liver cirrhosis or hepatocellular carcinoma.

[15] The medicament according to any of the items [10] to [14], wherein the PPARα agonist is (R)-2-[3-[[N-(benzoxazol-2-yl)-N-3-(4-methoxyphenoxy)propyl]aminomethyl]phenoxy]butyric acid or a salt thereof, or a solvate thereof.

[16] The medicament according to any of the items [10] to [15], wherein the SGLT2 inhibitor is selected from dapagliflozin, canagliflozin, ipragliflozin, empagliflozin, luseogliflozin, tofogliflozin, ertugliflozin, sotagliflozin, bexagliflozin or remogliflozin.

[17] The medicament according to any of the items [10] to [16], being a combination drug.

[18] The medicament according to any of the items [10] to [16], being a kit.

[19] A pharmaceutical composition for preventing and/or treating liver disease, including a PPARα agonist, an SGLT2 inhibitor and a pharmaceutically acceptable carrier.

[20] The pharmaceutical composition according to the item [19], wherein the liver disease comprises nonalcoholic fatty liver disease.

[21] The pharmaceutical composition according to the item [20], wherein the nonalcoholic fatty liver disease comprises nonalcoholic steatohepatitis.

[22] The pharmaceutical composition according to the item [20], having an effect to suppress hepatocyte ballooning in a subject with nonalcoholic fatty liver disease.

[23] The pharmaceutical composition according to the item [19], wherein the liver disease comprises liver cirrhosis or hepatocellular carcinoma.

[24] The pharmaceutical composition according to any of the items [19] to [23], wherein the PPARα agonist is (R)-2-[3-[[N-(benzoxazol-2-yl)-N-3-(4-methoxyphenoxy) propyl]aminomethyl]phenoxy]butyric acid or a salt thereof, or a solvate thereof.

[25] The pharmaceutical composition according to any of the items [19] to [24], wherein the SGLT2 inhibitor is selected from dapagliflozin, canagliflozin, ipragliflozin, empagliflozin, luseogliflozin, tofogliflozin, ertugliflozin, sotagliflozin, bexagliflozin or remogliflozin.

[26] A method for preventing and/or treating liver disease, including the process of administering to a subject in need of treatment an effective amount of a PPARα agonist and the process of administering to the subject an effective amount of an SGLT2 inhibitor.

[27] The preventing and/or treating method according to the item [26], wherein the liver disease comprises nonalcoholic fatty liver disease.

[28] The preventing and/or treating method according to the item [27], wherein the nonalcoholic fatty liver disease comprises nonalcoholic steatohepatitis.

[29] The preventing and/or treating method according to the item [27], for suppressing ballooning of hepatocytes in the subject with nonalcoholic fatty liver disease.

[30] The preventing and/or treating method according to the item [26], wherein the liver disease comprises liver cirrhosis or hepatocellular carcinoma.

[31] The preventing and/or treating method according to any of the items [26] to [30], wherein the PPARα agonist is (R)-2-[3-[[N-(benzoxazol-2-yl)-N-3-(4-methoxyphenoxy) propyl]aminomethyl]phenoxy]butyric acid or a salt thereof, or a solvate thereof.

[32] The preventing and/or treating method according to any of the items [26] to [31], wherein the SGLT2 inhibitor is selected from dapagliflozin, canagliflozin, ipragliflozin, empagliflozin, luseogliflozin, tofogliflozin, ertugliflozin, sotagliflozin, bexagliflozin or remogliflozin.

[33] The preventing and/or treating method according to any of the items [26] to [32], wherein the PPARα agonist and the SGLT2 inhibitor are simultaneously administered.

[34] The preventing and/or treating method according to any of the items [26] to [32], wherein the PPARα agonist and the SGLT2 inhibitor are separately administered at intervals.

[35] Use of a PPARα agonist and an SGLT2 inhibitor for manufacture of a prophylactic and/or therapeutic agent for liver disease.

[36] The use according to the item [35], wherein the liver disease comprises nonalcoholic fatty liver disease.

[37] The use according to the item [36], wherein the nonalcoholic fatty liver disease comprises nonalcoholic steatohepatitis.

[38] The use according to the item [36], wherein the agent has an effect to suppress hepatocyte ballooning in a subject with nonalcoholic fatty liver disease.

[39] The use according to the item [35], wherein the liver disease comprises liver cirrhosis or hepatocellular carcinoma.

[40] The use according to any of the items [35] to [39], wherein the PPARα agonist is (R)-2-[3-[[N-(benzoxazol-2-yl)-N-3-(4-methoxyphenoxy)propyl]aminomethyl]phenoxy]butyric acid or a salt thereof, or a solvate thereof.

[41] The use according to any of the items [35] to [40], wherein the SGLT2 inhibitor is selected from dapagliflozin, canagliflozin, ipragliflozin, empagliflozin, luseogliflozin, tofogliflozin, ertugliflozin, sotagliflozin, bexagliflozin or remogliflozin.

[42] The use according to any of the items [35] to [41], wherein the agent is a combination drug.

[43] The use according to any of the items [35] to [41], wherein the agent is a kit.

[44] A combination of a PPARα agonist with an SGLT2 inhibitor for preventing and/or treating liver disease.

[45] The combination according to the item [44], wherein the liver disease comprises nonalcoholic fatty liver disease.

[46] The combination according to the item [45], wherein the nonalcoholic fatty liver disease comprises nonalcoholic steatohepatitis.

[47] The combination according to the item [45], having an effect to suppress hepatocyte ballooning in a subject with nonalcoholic fatty liver disease.

[48] The combination according to the item [44], wherein the liver disease comprises liver cirrhosis or hepatocellular carcinoma.

[49] The combination according to any of the items [44] to [48], wherein the PPARα agonist is (R)-2-[3-[[N-(benzoxazol-2-yl)-N-3-(4-methoxyphenoxy)propyl]aminomethyl]phenoxy]butyric acid or a salt thereof, or a solvate thereof.

[50] The combination according to any of the items [44] to [49], wherein the SGLT2 inhibitor is selected from dapagliflozin, canagliflozin, ipragliflozin, empagliflozin, luseogliflozin, tofogliflozin, ertugliflozin, sotagliflozin, bexagliflozin or remogliflozin.

[51] The combination according to any of the items [44] to [50], being a combination drug.

[52] The combination according to any of the items [44] to [50], being a kit.

Advantageous Effects of Invention

The therapeutic agent, medicament, pharmaceutical composition, treating method, use or combination of the present invention can suppress enlargement of lipid droplets in hepatocytes and/or ballooning of hepatocytes in a patient with nonalcoholic fatty liver disease (NAFLD) or nonalcoholic steatohepatitis (NASH). Accordingly, the present invention can provide new prevention and/or treatment of NAFLD and NASH. In particular, the present invention can provide prevention and/or treatment of highly severe NASH.

BRIEF DESCRIPTION OF DRAWINGS

FIG. 1 shows the lipid droplet size ($\mu m^2$) in hepatocytes when Compound 1 (0.1 mg/kg), tofogliflozin (10 mg/kg) or a combination of Compound 1 (0.1 mg/kg) and tofogliflozin (10 mg/kg) of the present invention is administered.

FIG. 2 shows ballooning of hepatocytes when Compound 1 (0.1 mg/kg), tofogliflozin (10 mg/kg) or a combination of Compound 1 (0.1 mg/kg) and tofogliflozin (10 mg/kg) of the present invention is administered.

FIG. 3 shows ballooning of hepatocytes when Compound 1 (0.1 mg/kg), ipragliflozin (3 mg/kg) or a combination of Compound 1 (0.1 mg/kg) and ipragliflozin (3 mg/kg) of the present invention is administered.

DESCRIPTION OF EMBODIMENTS

In the present invention, PPARα agonist means a generic term of compounds activating a PPARα-type receptor. PPARα-type receptor is a type of peroxisome proliferator-activated receptors (PPAR) which are one kind of nuclear receptors. PPARα-type receptor involves in fat oxidation. Specifically included are fibrates such as fenofibrate, clofibrate, bezafibrate, clinofibrate, ciprofibrate, etofibrate and gemfibrozil, and WY-14643 (pirinixic acid), GW-7647 (2-(4-(2-(1-(1-cyclohexane butyl)-3-cyclohexylureido)ethyl) phenylthio)-2-methylpropionate), and pemafibrate. (R)-2-[3-[[N-(benzoxazol-2-yl)-N-3-(4-methoxyphenoxy)propyl] aminomethyl]phenoxy]butyric acid (Compound 1), which is also known as the common name pemafibrate, is used in the present invention. It can be produced, for example, according to the method described in WO 2005/023777 or according to any publicly known method described in documents.

In the present invention, SGLT2 inhibitor means a generic term of compounds having an inhibitory effect on a sodium glucose cotransporter 2 (SGLT2) involved in glucose reabsorption in the kidney. Specifically included are dapagliflozin, canagliflozin, ipragliflozin (ASP1941), empagliflozin (BI 10773), luseogliflozin (TS-071), tofogliflozin (CSG452), ertugliflozin (PF-04971729), sotagliflozin (LX-4211), bexagliflozin (EGT-1442) and remogliflozin (KGT-1681). Each of these compounds may be used as a pharmaceutically acceptable salt and/or solvate as appropriate, but the present invention includes all of them.

Ipragliflozin is a common name for a compound (1S)-1,5-anhydro-1-C-{3-[(1-benzothiophen-2-yl)methyl]-4-fluorophenyl}-D-glucitol. Ipragliflozin can be used, for example, as ipragliflozin L-proline (1:1).

Tofogliflozin is a common name for a compound (1S,3'R,4'S,5'S,6'R)-6-[(4-ethylphenyl)methyl]-6'-(hydroxymethyl)-3',4',5',6'-tetrahydro-3H-spiro[2-benzofuran-1,2'-pyran]-3',4',5'-triol. Tofogliflozin can be used, for example, as tofogliflozin monohydrate.

Ipragliflozin can be produced, for example, according to the method described in WO 2004/080990 or according to any publicly known method described in documents.

Tofogliflozin can be produced, for example, according to the method described in WO 2006/080421 or according to any publicly known method described in documents.

In the present invention, the liver disease includes fatty liver, hepatitis, NAFLD, NASH, liver cirrhosis and liver cancer such as hepatocellular carcinoma.

The "salt" of the present invention is not particularly limited as long as it is pharmaceutically acceptable. It includes alkali metal salts such as sodium salt and potassium salt; alkaline earth metal salts such as calcium salt and magnesium salt; inorganic base salts such as ammonium salt; organic base salts such as trialkylamine salt; mineral acid salts such as hydrochloride salt and sulfate salt; and organic acid salts such as acetate salt.

The "solvate" of the present invention includes a hydrate and alcoholate (such as ethanolate).

A combination drug is a pharmaceutical product including two or more active ingredients in a single dosage form. In the present invention, an example of the combination drug may be a tablet including the PPARα agonist and the SGLT2 inhibitor in an effective amount.

A kit is a set of two or more pharmaceutical products. Each of the pharmaceutical products may be taken or administered simultaneously or separately at intervals. In the present invention, an example of the kit may be a combination of a pharmaceutical product containing an effective amount of the PPARα agonist with a pharmaceutical product containing an effective amount of the SGLT2 inhibitor.

NASH is characterized by hepatocyte ballooning in addition to enlargement of lipid droplets in hepatocytes (see Non-Patent Documents 3 and 6). As described in the Examples below, the combined use of Compound 1 with ipragliflozin significantly inhibited ballooning of hepatocytes in a NASH-HCC mouse that is a model animal for NASH. In addition, the combined use of Compound 1 with tofogliflozin significantly inhibited ballooning of hepatocytes in a NASH-HCC mouse and inhibited enlargement of lipid droplets in the hepatocytes. Accordingly, the combined use of the PPARα agonist with the SGLT2 inhibitor of the present invention is useful as a prophylactic and/or therapeutic agent for NASH in mammals including humans.

The therapeutic agent, medicament and the like obtained by combining the PPARα agonist with the SGLT2 inhibitor of the present invention can be used alone or in combination with other pharmaceutically acceptable carriers to prepare a dosage form such as tablets, capsules, granules, powders, lotions, ointments, injections or suppositories. These preparations can be produced according to a known method.

The therapeutic agents, medicaments and the like obtained by combining the PPARα agonist with the SGLT2 inhibitor of the present invention are administered orally or parenterally. Those skilled in the art can appropriately set the dose depending on the body weight, age, sex, symptom and the like of a patient. When Compound 1 as a PPARα agonist is administered to an adult, the daily dose may range from 0.01 to 1000 mg, preferably from 0.01 to 10 mg, more preferably from 0.05 to 5 mg, and it is administered preferably in 1 to 3 divided doses. When ipragliflozin is used as an SGLT2 inhibitor, the daily dose may range from 0.1 to 1000 mg, preferably from 1 to 200 mg. When tofogliflozin is used as the SGLT2 inhibitor, the daily dose may range from 0.1 to 500 mg, preferably from 1 to 100 mg. In either case, the daily dose is administered in 1 to 3 divided doses.

EXAMPLES

Hereinafter, the present invention is described more specifically with reference to Examples, but the present invention is not limited to the Examples at all.

Example 1 Effect of Compound 1 Combined with Tofogliflozin on NASH Mouse Model

A NASH-HCC mouse is a model animal that develops liver cirrhosis from fatty liver via NASH when it is fed with a high fat diet, and subsequently develops hepatocellular carcinoma (Non-Patent Document 9). The effect of compound 1 combined with tofogliflozin was examined using the NASH-HCC mouse model.

In this examination, Compound 1 was prepared according to the method described in the Patent Document 1. Tofogliflozin monohydrate (Chugai Pharmaceutical Co., Ltd.) was used as a concrete example of tofogliflozin.

1) Used Animal:

NASH-HCC mice were prepared with reference to Non-Patent Document 9, and were used for this experiment. Specifically, male C57BL/6J mice were subcutaneously administered 200 μg of streptozotocin on the second day after birth. The mice were fed ad libitum with a high-fat diet (HFD-32, Clea Japan, Inc.) for 2 weeks starting from 4-week-old. The mice were separated into four groups as described in below 2) and were administered drugs from 6-week-old to 9-week-old as described in below 3). Daily food consumption of the mice in each group were measured while the drugs were administered so that the mice of all groups were fed with the same amount of food as those for the control group.

2) Manner of Grouping:

NASH-HCC mice were separated into four groups which included a control group, a group administered 0.1 mg/kg of Compound 1, a group administered 10 mg/kg of tofogliflozin and a group administered in their combination (0.1 mg/kg of Compound 1 and 10 mg/kg of tofogliflozin) (n=5 to 7). The mice were separated immediately before starting drug administration (at 6-week-old). There was no difference in the mean of body weight between the groups.

3) Drug Administration:

The control group was administered 3% gum arabic aqueous solution. Compound 1 and/or tofogliflozin was dissolved in 3% gum arabic aqueous solution, and was administered to the group administered Compound 1, the group administered tofogliflozin or the group administered in their combination, respectively. The mice of each group were orally administered the solution in 5 mL/kg body weight once a day. The administration period was for 3 weeks starting from 6-week-old as described above.

4) Method of Observation and Examination:

After the administration period, the liver of each mouse was excised under anesthesia and was fixed with 10% neutral buffered formalin solution to prepare hematoxylin-eosin stained specimens. Using the specimens, the lipid droplet size in hepatocyte was analyzed by image analysis software Image J. The area of 6000 to 10,000 lipid droplets was measured in each specimen. The median of the lipid droplet area was calculated for each mouse and then the median and quartile were calculated for each group based on the median for each mouse in the group. These data were expressed in a box-and-whisker plot (FIG. 1).

Ballooning of hepatocytes in each mouse was scored under blind conditions according to the following criteria (Kleiner et al., Hepatology 41, 1313-21, 2005).

No balloon cells: 0

Balloon cell is rare (Few balloon cells): 1

Many Balloon cells or prominent (Ballooning): 2 Then, the mean value of the scores (ballooning score) was calculated in each group and the values were shown (FIG. 2).

Statistical processing was performed using statistical software EZR, which extends the functions of R and R commander. The software is distributed free of charge on the website of Jichi Medical University Saitama Medical Center (Bone Marrow Transplantation (2013) 48, 452-458). The Steel test (N=5 to 7) was performed using EZR, the drug administration group was labeled with the mark * in figures when the group had the significant difference at $p<0.05$ with respect to the control group, and labeled with the mark ** when the group had the significant difference at $p<0.01$.

5) Result

As shown in FIG. 1, the median of lipid droplet size was 1.17 ($\mu m^2$) in the control group, 1.00 ($\mu m^2$) in the group administered 0.1 mg/kg of Compound 1 and 1.00 ($\mu m^2$) in the group administered 10 mg/kg of tofogliflozin. Although there was a tendency of the size of lipid droplets in hepatocytes to decrease, there was no statistically significant difference. In contrast with the single administration groups, the median of lipid droplet size was 0.89 ($\mu m^2$) in their combination use group, and a significant decrease (p=0.037) was observed with respect to the control group.

In addition, as shown in FIG. 2, the ballooning score was 1.33 in the control group, 0.60 in the group administered 0.1 mg/kg of Compound 1 and 0.71 in the group administered 10 mg/kg of tofogliflozin. Although there was a tendency of ballooning of hepatocytes to be suppressed, there was no statistically significant difference. In contrast with the single administration groups, the ballooning score was 0.14 in their combination use group, and a marked suppression (p=0.0089) of ballooning of hepatocytes was observed with respect to the control group.

Example 2 Effect of Compound 1 Combined with Ipragliflozin on NASH Mouse Model

The effect of Compound 1 combined with ipragliflozin was examined in NASH-HCC mice (Non-Patent Document 9).

In this examination, Compound 1 was prepared according to the method described in the Patent Document 1. Ipragliflozin (Shanghai Haoyuan Chamexpress Co., Ltd., Shanghai, China) was used as a concrete example of ipragliflozin.

1) Used Animals:

NASH-HCC mice were prepared in the same manner as in 1) of Example 1, and were used for this experiment.

2) Manner of Grouping:

NASH-HCC mice were separated into four groups which included a control group, a group administrated 0.1 mg/kg of Compound 1, a group administrated 3 mg/kg of ipragliflozin and a group administrated in their combination (0.1 mg/kg of Compound 1 and 3 mg/kg of ipragliflozin) (n=8). The mice were separated immediately before starting drug administration (at 6-week-old). There was no difference in the mean of body weight between the groups.

3) Drug Administration:

The control group was administered 3% gum arabic aqueous solution. Compound 1 and/or ipragliflozin was dissolved in 3% gum arabic aqueous solution, and was administered to the group administered Compound 1, the group administered ipragliflozin or the group administered in their combination, respectively. The mice of each group were orally administered the solution in 5 mL/kg body weight once a day. The administration period was for 3 weeks starting from 6-week-old.

4) Method of Observation and Examination:

Observation and examination was carried out in the same manner as in 4) of Example 1.

5) Result

As shown in FIG. 3, the ballooning score was 1.50 in the control group, 1.35 in the group administrated 0.1 mg/kg of Compound 1 and 0.88 in the group administrated 3 mg/kg of ipragliflozin. Although there was a tendency of ballooning of hepatocytes to be suppressed, there was no statistically significant difference. In contrast with the single administration group, the ballooning score was 0.38 in their combined use group, and a marked suppression (p=0.009) of ballooning of hepatocytes was observed with respect to the control group.

As is evident from the above results, a combined use of Compound 1 with an SGLT2 inhibitor such as tofogliflozin or ipragliflozin of the present invention provides a remarkable effect to reduce lipid droplet size in hepatocytes and to suppress ballooning of hepatocytes in the NASH mouse model. Reduction of lipid droplet size in hepatocytes and suppression of ballooning of hepatocytes correspond to improvement of the condition of NAFLD and NASH, which in turn leads to prevention of liver cirrhosis and hepatocellular carcinoma that are terminal diseases of NAFLD and NASH.

INDUSTRIAL APPLICABILITY

Since a combination of a PPARα agonist and an SGLT2 inhibitor exhibits a prophylactic and/or therapeutic effect on NAFLD and NASH, the present invention has industrial applicability.

The invention claimed is:

1. A method for treating a liver disease in a human subject suffering from a liver disease selected from nonalcoholic fatty liver disease, nonalcoholic steatohepatitis, liver cirrhosis, and hepatocellular carcinoma, the method comprising: administering to the subject therapeutically effective amounts of pemafibrate or a pharmaceutically acceptable salt thereof and tofogliflozin or a pharmaceutically acceptable salt thereof, wherein the therapeutic effective amounts treat the liver disease.

2. The method of claim 1 wherein the liver disease is nonalcoholic fatty liver disease.

3. The method of claim 1 wherein the liver disease is nonalcoholic steatohepatitis.

4. The method of claim 1 wherein the liver disease is liver cirrhosis.

5. The method of claim 1 wherein the liver disease is hepatocellular carcinoma.

6. The method of claim 1 wherein the subject is identified as suffering from the liver disease.

7. A method for reducing lipid droplet size and ballooning in the liver of a human subject suffering from a liver disease selected from nonalcoholic fatty liver disease, nonalcoholic steatohepatitis, liver cirrhosis, and hepatocellular carcinoma, the method comprising: administering to the subject therapeutically effective amounts of pemafibrate or a pharmaceutically acceptable salt thereof and tofogliflozin or a pharmaceutically acceptable salt thereof, wherein the therapeutic effective amounts reduce the lipid droplet size and ballooning.

8. The method of claim 7, wherein the liver disease is nonalcoholic fatty liver disease.

9. The method of claim 7, wherein the liver disease is nonalcoholic steatohepatitis.

10. The method of claim 7, wherein the liver disease is liver cirrhosis.

11. The method of claim 7, wherein the liver disease is hepatocellular carcinoma.

\* \* \* \* \*